United States Patent
Mohr

[11] Patent Number: 6,144,211
[45] Date of Patent: Nov. 7, 2000

[54] CROSS-CHANNEL PROBE SYSTEM FOR TIME DOMAIN REFLECTOMETRY DETECTION OF FLUID FLOW

[76] Inventor: Charles L. Mohr, 1440 Agnes St., Richland, Wash. 99352

[21] Appl. No.: 09/105,302

[22] Filed: Jun. 25, 1998

[51] Int. Cl.[7] .................................................. G01R 27/04
[52] U.S. Cl. .................................... 324/642; 324/643
[58] Field of Search ..................... 324/439, 446, 324/642, 663, 676, 633, 686, 693, 710, 772; 73/61.61, 866.5, 861.28

[56] References Cited

U.S. PATENT DOCUMENTS

| | | |
|---|---|---|
| 3,424,002 | 1/1969 | Johnson . |
| 3,474,337 | 10/1969 | Petrick . |
| 3,572,119 | 3/1971 | Bak . |
| 3,626,284 | 12/1971 | Bak . |
| 3,695,107 | 10/1972 | Hertz et al. . |
| 3,832,900 | 9/1974 | Ross . |
| 3,853,005 | 12/1974 | Schendel . |
| 3,922,914 | 12/1975 | Fuchs . |
| 3,995,212 | 11/1976 | Ross . |
| 4,135,397 | 1/1979 | Krake . |
| 4,170,135 | 10/1979 | Booman et al. . |
| 4,345,202 | 8/1982 | Nagy et al. . |
| 4,453,125 | 6/1984 | Kimura et al. . |
| 4,495,807 | 1/1985 | Field et al. . |
| 4,510,437 | 4/1985 | Iskander . |
| 4,786,857 | 11/1988 | Mohr . |
| 4,807,471 | 2/1989 | Cournane et al. . |
| 4,922,180 | 5/1990 | Saffer et al. . |
| 4,961,147 | 10/1990 | Moore ..................................... 324/446 |
| 5,495,176 | 2/1996 | Shiranita et al. ....................... 324/439 |
| 5,554,936 | 9/1996 | Mohr . |
| 5,723,979 | 3/1998 | Mohr ..................................... 324/642 |
| 5,748,002 | 5/1998 | Scott et al. .............................. 324/633 |

*Primary Examiner*—Safet Metjahic
*Assistant Examiner*—Vincent Q. Nguyen
*Attorney, Agent, or Firm*—Wells, St. John, Roberts, Gregory & Matkin, P.S.

[57] ABSTRACT

A sensor system for use with time domain reflectometry systems to allow measurement of relative proportions of intermixed constituents having differing electrical permittivities contained in a fluid mixture. The sensor comprises at least one primary electrode and one secondary electrode which are spaced apart across a flow channel. One electrode is connected to a first conductor carrying the active time domain reflectometry signal pulse. The other electrode is connected to the passive or ground conductor which carries any reactive signal resulting from the active signal. A fluid mixture of variable proportions will demonstrate a variable dielectric constant which affects the reflected signals sensed by the time domain reflectometer.

36 Claims, 5 Drawing Sheets

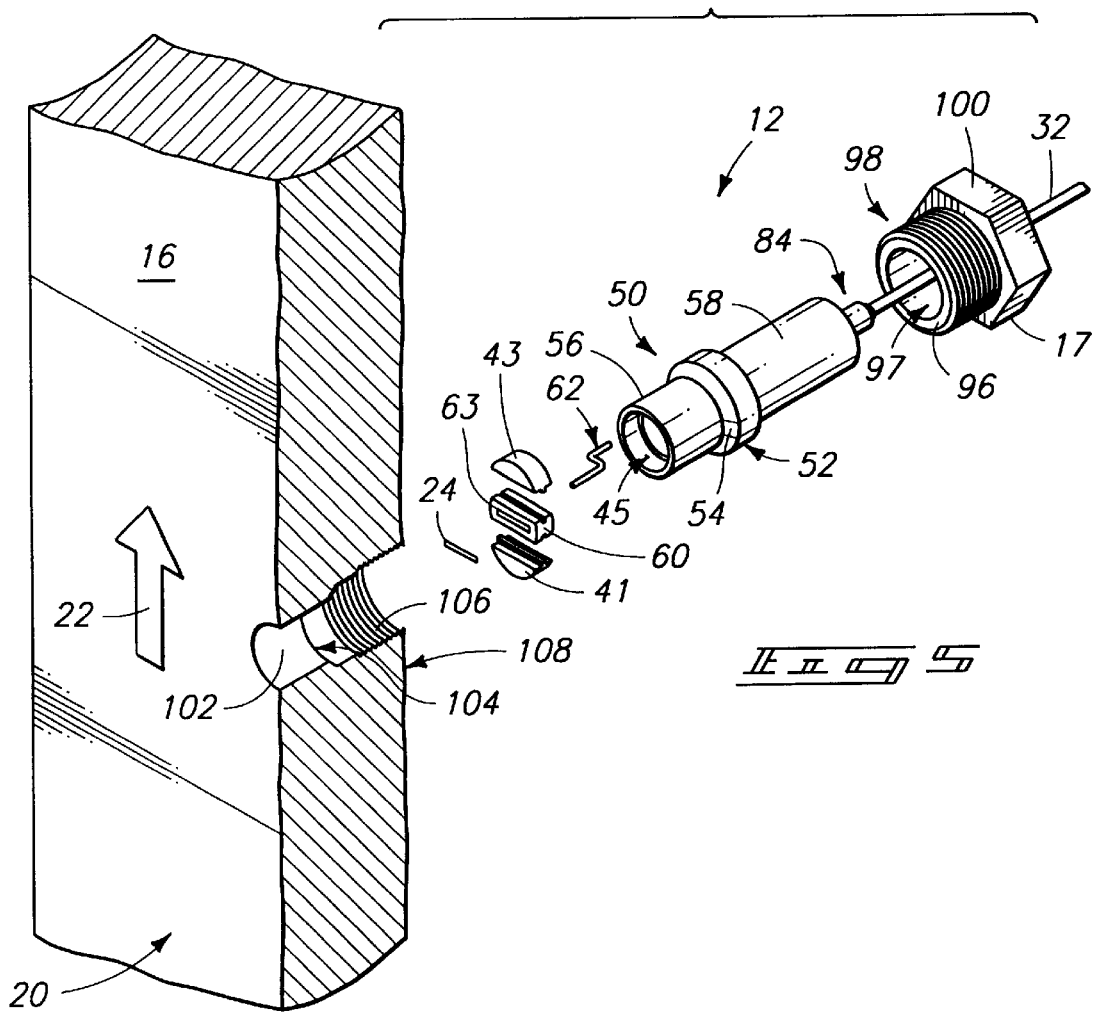
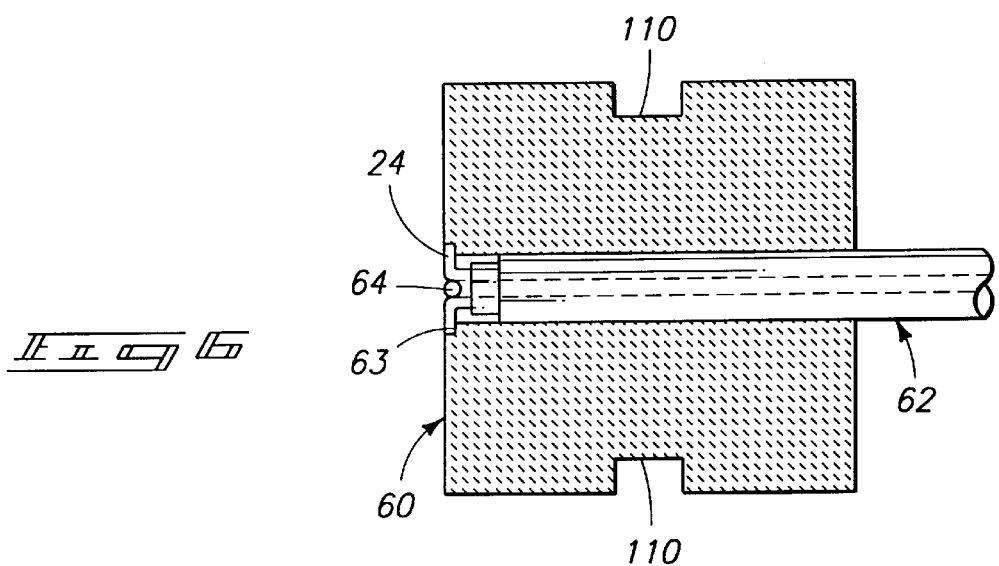

CROSS-CHANNEL PROBE SYSTEM FOR TIME DOMAIN REFLECTOMETRY DETECTION OF FLUID FLOW

TECHNICAL FIELD

The technical field of this invention is sensing apparatus used with time domain reflectometry systems to determine the relative proportions of mixed fluids, particularly mixed liquid and gaseous phases, for example mixtures of water and steam.

BACKGROUND OF THE INVENTION

Time domain reflectometry has been previously known effective in methods for determining the level of a liquid, such as in a tank. According to such time domain reflectometry methods, electrical pulses are conveyed along a transmission line to an electrically conductive probe extending over the range of liquid levels being detected. The stimulating electrical pulses produced in the time domain reflectometry system are partially reflected at the vapor-liquid interface due to a change in the electrical impedance. The impedance change is associated with the differences in the dielectric strength between the liquid and the overlying gas or vapor. The electrical permittivity is the technical term indicating the dielectric properties of the fluids involved.

The electrical pulses produced by a time domain reflectometry system are affected by the dielectric constant of the surrounding media in which the signal is traveling. The dielectric constant (permittivity) of the adjacent media directly affects the propagation velocity of an electromagnetic wave as it travels along the transmission line and along any attached probe or sensor. In time domain reflectometry systems, a fast rise time electromagnetic pulse is propagated along a transmission line having a known length while measuring the time of arrival and the time of reflections from electrical discontinuities in the transmission line at two known, spaced points. One known, spaced point is located where a coaxial connecting cable of the transmission line is attached to the transmission line probe. The other known, spaced point is located at the distal end of the transmission line probe. Since these locations are both known, one can calculate the propagation velocity of the electromagnetic wave and, as a result, calculate the apparent dielectric constant of the material undergoing tests and through which the transmission line probe extends. Similarly, changes in the dielectric constant which relate to changes in the media adjacent the probe can also be determined. For example, the apparent dielectric constant may provide a direct indication of the presence of water versus the presence of water vapor or air.

U.S. Pat. No. 4,786,857 to Charles L. Mohr, et al., entitled "Methods and Apparatus for Time Domain Reflectometry Determination of Relative Proportion, Fluid Inventory and Turbulence", disclosed apparatus and methods for using time domain reflectometry to determine the relative proportions of intermixed constituents in a fluid system. Such apparatus and methods can be used to determine the relative proportions of liquid and vapor even when the liquid and vapor are intermixed either homogeneously or non-homogeneously. Measurement capabilities such as these are particularly valuable to the process industries and nuclear energy production. The systems can be used to monitor nuclear reactor coolant systems, in which the total inventory of system coolant, including intermixed water and steam, must be determined under a variety of conditions, including even accident conditions. Methods are also described for obtaining indications of turbulence in fluid mixtures by measuring variations in fluid properties over time.

The above-mentioned Mohr patent disclosed a probe including an inner centrally located electrode mounted within a cylindrical outer electrode. The cylindrical outer electrode was provided with slots to allow fluid to pass into the annular volume between the inner and the outer electrodes. The probe was immersed in the mixed-constituent system. The average dielectric constant or permittivity experienced by the electrical pulse transiting the probe was determined using time domain reflectometry. The measured permittivity was then correlated with known characteristic data of the constituents being measured to determine their relative proportions.

U.S. Pat. No. 5,554,936, also to Charles L. Mohr, et al., entitled "Mixed Fluid Time Domain Reflectometry Sensors", disclosed apparatus in the form of improved probe sensors which could be used for a greater variety of applications and still provide measurements. More particularly, there was a need to provide a probe that was more effective when used in some applications, particularly in applications where solutions rich in minerals, such as from earth wells, were not capable of measurement. Accordingly, the improved probe sensor was capable of service under a variety of conditions with accuracy and reliability.

The probe shown in U.S. Pat. No. 5,554,936 has been found less than satisfactory when used in some situations. One situation is when the probe is required to be placed directly within the flow path of a fluid flow channel. Placement of the probe sensor directly across a flow channel subjects the probe to pressures from fluid flow, increases the risk of damage from the flowing fluid and materials present within such flow. Placement across a flow channel also requires that the probe sensor be removed during cleaning operations of the fluid flow channel in order to prevent damage to such probe. The current invention addresses the need for improved time domain reflectometry probes which are capable of service under a greater variety of conditions in fluid flow channels, with accuracy and reliability.

BRIEF DESCRIPTION OF THE DRAWINGS

One or more preferred forms of the invention are described herein with reference to the accompanying drawings. The drawings are briefly described below.

FIG. 5 is an exploded perspective view of one sensor forming part of the system of FIGS. 1–4.

FIG. 6 is a partial sectional view taken along line 6—6 of FIG. 2.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

Figure 1:
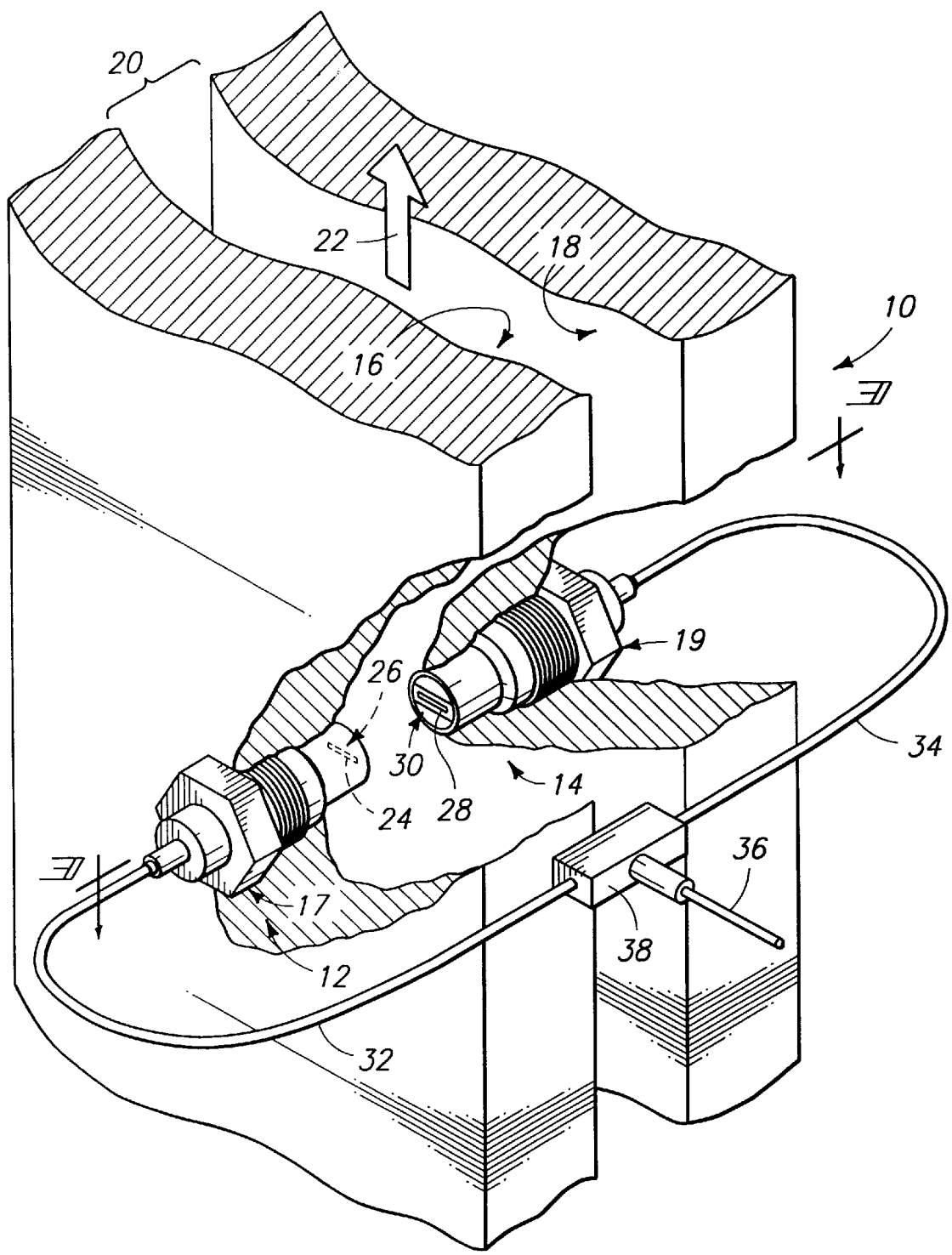
FIG. 1 is a perspective view of a time domain reflectometry sensor system for measuring flow characteristics in accordance with a first preferred embodiment of the invention.

FIG. 1 illustrates a time domain reflectometry cross-channel probe or sensor system 10 in accordance with a preferred embodiment of the invention. The probe or sensor system 10 is intended to be used with time domain reflectometry systems to allow measurement of relative proportions of intermixed constituents having differing electrical permittivities contained in a fluid mixture. An example of such a time domain reflectometry system is described in U.S. Pat. No. 4,786,857 to Charles L. Mohr, entitled "Methods and Apparatus for Time Domain Reflectometry Determination of Relative Proportion, Fluid Inventory and Turbulence", which is hereby incorporated by reference in its entirety. Another example of sensors for use in such a time domain reflectometry system is described in U.S. Pat. No. 5,554,936, also to Charles L. Mohr, entitled "Mixed Fluid Time Domain Reflectometry Sensors", which is also hereby incorporated by reference in its entirety.

Probe or sensor system 10 advantageously includes a pair of probes or sensors 12 and 14 supported in opposing walls 16 and 18. Walls 16 and 18 form parts of a fluid flow channel 20 in which a fluid mixture 22 is contained. More specifically, walls 16 and 18 form fluid guiding or containing walls that partially define fluid flow channel 20.

Probe 12 supports a primary electrode 24 in fluid channel-forming wall 16. In the preferred construction shown, the inside face of electrode 24 has a sensing surface 26. The inside face of electrode 24 is positioned adjacent to fluid mixture 22. The inside face can either be immediately adjacent to the fluid mixture or separated by a thin dielectric layer. It is preferable to use a thin dielectric layer to reduce signal loss, particularly when the flow channel contains fluids which are electrically conductive, or contain ions which can electrically affect the signal applied to the electrode. The inside face is most preferably in approximately level relationship with the associated channel-forming wall 16. Primary electrode 24 is supported in electrically isolated relationship within wall 16.

Secondary electrode 28 is supported in an electrically isolated condition within wall 18 in a fashion similar to electrode 24. Secondary electrode 28 is also spaced and electrically isolated from primary electrode 24. Secondary electrode 28 is supported in wall 18 such that a sensing surface 30 is supported adjacent to fluid mixture 22 in substantially level relation with the associated channel-forming wall 18.

The primary and secondary electrodes are preferably positioned in face-to-face opposing relationship. In the preferred configuration shown, primary electrode 24 and secondary electrode 28 are each formed in the shape of elongated pieces having longitudinal axes 53 (FIG. 2) which for both electrodes are oriented in the same plane. Each of electrodes 24 and 28 also advantageously has a local recess and aperture for facilitating electrical connection with accompanying electrical conductors (see FIG. 6 at conductor 64). Other connection constructions are also possible.

The fluid mixture 22 or other composition being measured is interposed between primary electrode 24 and secondary electrode 28. In many instances, this will involve a moving fluid which is interposed between these electrodes. One instance of use is in the measuring of relative proportions of intermixed constituents within a flowing fluid mixture 22. It is important to note that primary electrode 24 and secondary electrode 28 are mounted within walls 16 and 18, respectively, in a manner which does not inhibit or impede fluid flow of fluid mixture 22 within fluid flow channel 20. Hence, fluid flow characteristics are not impeded by the presence of probe system 10 along channel 20. This also facilitates maintenance and cleaning of channel 20 without requiring the removal of probe system 10 therefrom.

Fluid channel walls 16 and 18 are presented in a substantially parallel configuration such that probes 12 and 14 are mounted in a substantially co-linear relation. In such a relationship, the primary electrode 24 and secondary electrode 28 are in complementary and opposing positions along opposite sides of fluid flow channel 20. It is to be understood that additional fluid channel-forming walls are provided for joining together walls 16 and 18, but are not shown here, so as to encircle channel 20 and contain fluid mixture 22 inside channel 20. One common implementation includes a single cylindrical pipe or duct, with probes 12 and 14 being provided in complementary and opposing wall portions. This allows the probe system to detect the electrical permittivity of constituents of fluid mixture 22, such as when such constituents are flowing by and between the opposing probe faces. In this manner or any of a number of other cross-channel configurations, the probe system 10 of this invention can be utilized.

According to the probe construction of probe system 10 and as shown in FIG. 1, fluid mixture 22 is interposed between probes 12 and 14 so as to provide, at least in part, a dielectric layer therebetween. Preferably, a separate dielectric face layer is also provided on probes 12 and 14. The face layer can be formed as a coating upon the inward faces of primary electrode 24 and secondary electrode 28. The dielectric face layer covers the sensing surfaces 26 and 30, respectively. Details of such a coating system are described below with reference to FIG. 2.

Figure 3:
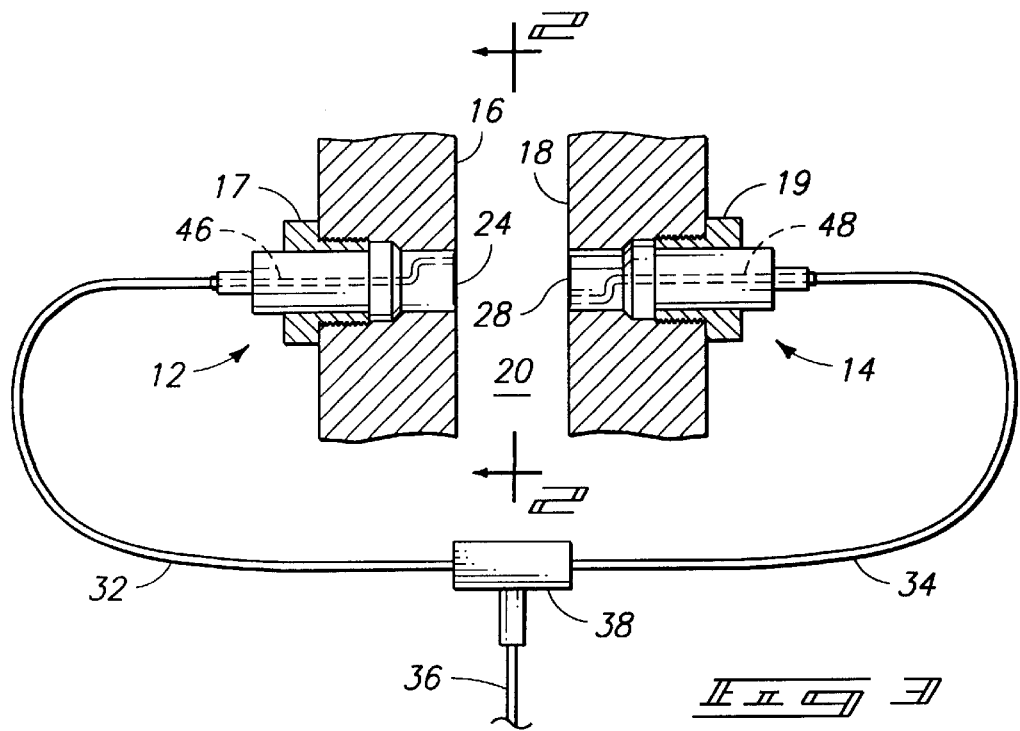
FIG. 3 is a simplified schematic and partial sectional plan view illustrating sensors and other key parts of the system of FIG. 1.

As shown in FIGS. 1 and 3, channel probe system 10 includes a pair of substantially matched lead lines 32 and 34. Probes 12 and 14 are connected in parallel with a signal main line 36 via a tee connector 38. Signal main line 36 supplies a time domain reflectometry pulse via tee connector 38 to lead lines 32 and 34 and to probes 12 and 14. The central or first conductor of the signal main line is connected to the central conductors of both lead lines 32 and 34. The outer or second conductor of the main signal line 36 is connected to the outer or second conductors of lead lines 32 and 34. In the preferred arrangement of this invention, the primary electrode 24 is connected to the center conductor of lead 32, whereas the secondary electrode 28 is connected to the outer or second conductor of lead line 34. This provides an opposing polarity relationship between the primary electrode 24 and secondary electrode 28.

Lead lines 32 and 34, main signal line 36, tee connector 38, and electrical portions of probes 12 and 14, including electrodes 24 and 28, are preferably constructed and sized so as to substantially impedance match the components. Impedance matching minimizes the occurrence of any spurious or unwanted impedance-induced signal reflections resulting from a signal being transmitted therethrough. Additionally, by substantially matching the lengths of lead lines 32 and 34, the resultant timing of signal delivery to and from electrodes 24 and 28 will be matched.

In operation, secondary electrode 28 is connected to the second, passive, or ground conductor of signal line 36. Primary electrode 24 is connected with the primary or active signal conductor of line 36. Lines 32, 34 and 36 can also include a third and outer shield conductor which is provided merely to shield both the active and passive signal conductors from undesirable electrical field interference and thus minimize errors from stray electromagnetic sources.

Secondary electrode 28 of probe 14 produces a ground reaction which reacts or interacts with the active pulse from primary electrode 24. When the active pulse and reactive pulse reach the electrodes 24 and 28, this develops a field across the fluid mixture within channel 20. The signal pulses propagate at a very high speed, so the matching of cable length on lines 32 and 34 is essential to monitoring the reflected signals which result from the field and impedance experienced across the channel between electrodes 24 and 28.

It is also desirable to impedance match essentially all of the components of system 10. To implement this, it is also preferable to match impedances at tee 38 and lines 32 and 34 versus the impedance along line 36. Signal line 36 is preferably provided with a 50-ohm nominal line impedance. Signal line 36 connects with a signal processor to deliver a signal pulse to system 10. The stimulating signal pulse is driven down the 50-ohm main signal line 36 and is then split at tee connector 38. Preferably, lead lines 32 and 34 ideally each have a 100-ohm line impedance in order to provide in parallel an effective impedance which matches or nearly matches the 50-ohm signal line. However, the bulk of commercially available low-cost coaxial lines typically have line impedances in the range of 80–90 ohms, and such a degree of matching has been found acceptable. For those applications where cost is a consideration, such lines will prove suitable when attempting to substantially impedance match the signal lines connected to electrodes 24 and 28. By driving a pulse down the 50-ohm signal line 36 and splitting it at tee connector 38, an effective impedance of approximately 40 ohms results. The resulting active and reactive pulses both transit along branch lines 32 and 34.

Probe 14 is coupled with the ground lead by a metal outer sheath of line 34. The active lead of line 32 is advantageously provided by the center conductor of line 32, and is coupled with primary electrode 24 of primary probe 12. The secondary conductor of line 32 is not connected to any of the sensory components of probe 12, but instead dead-ends at a point removed from the sensor 24 electrode. Conversely, the center conductor on lead line 34 is not connected to any of the sensory components of probe 14. It also dead-ends at a point removed from the sensing electrode 28. Further details of such arrangement are shown with respect to FIG. 3.

As shown on FIGS. 1 and 3, bifurcated lead lines 32 and 34, signal line 36, and tee connector 38 comprise coaxial electrical signal cabling components. In this manner, each of probes 12 and 14 is preferably connected to a coaxial electrical signal lead such as coaxial cables 32 and 34, respectively. Coaxial cables 32 and 34 each have a central, or inner, conductor and a secondary conductor which can be in the form of an outer conductor 48 (see FIG. 4). Alternatively, and more preferably, the secondary conductor can be sheathed by a third shielding layer outside of the secondary conductor.

Primary conductor 46 of lead line, or cable, 32 is electrically connected to primary electrode 24 of probe 12. Outer sheathing 48 of lead line, or cable, 34 is electrically connected to secondary electrode 28 of probe 14. Because probes 12 and 14 are contemplated for use in a high temperature environment, the cables of lines 32, 34 and 36 have a stainless steel outer sheathing, silica insulation, and copper primary and secondary conductors. This design for lead lines 32, 34 and 36 is sometimes referred to as "hardline" coaxial cable.

Figure 4:
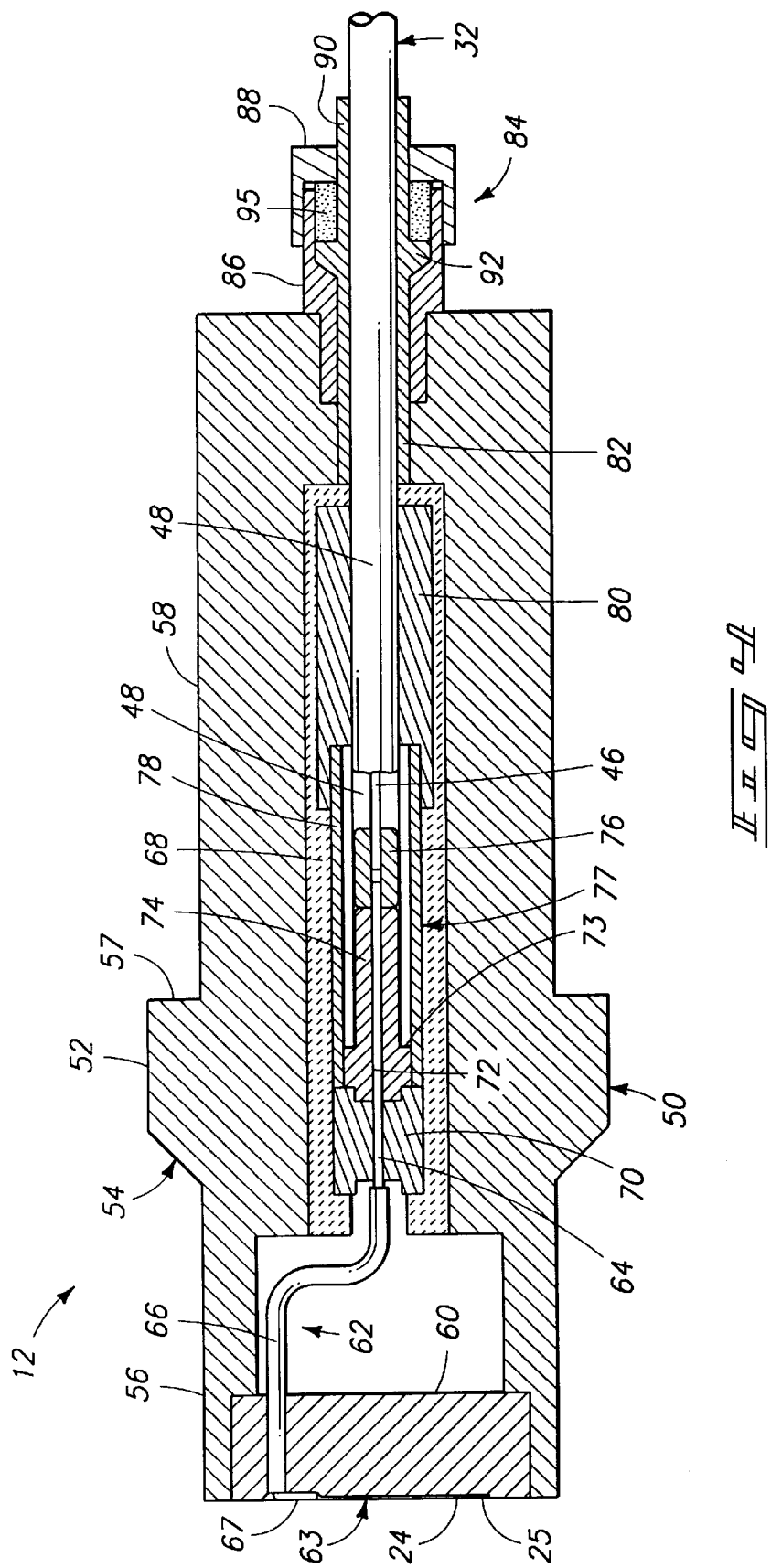
FIG. 4 is an enlarged longitudinal sectional view taken along section line 4—4 of FIG. 2.

A time domain reflectometry active signal has a very sharp rise and drop in voltage. This is transmitted along the central conductor to primary electrode 24 of probe 12. The active signal experiences a detectible change in impedance where the secondary conductor 48 ends within the probe housing 50. More specifically, this occurs at the shoulder 73 of part 74 as shown in FIG. 4. The permittivity at this point changes and the time domain reflectometry detection system will show a noticeable change. This point thus serves as a reference which serves to help delineate between the line portion of the time domain reflectometer range and a transition portion. The transition portion extends from such point outwardly to the connection with the electrode 24. Other signal reference points can also be used if there is a sufficient detectable impedance change. For example, the proximate end of the electrode is connected to conductor 64 at a point which may give rise to a detectible impedance change. In prior testing, this point has not been as easily identified in the time domain reflectometry scans as is the terminus of the secondary conductor near shoulder 73. These or other points along the electrical path can be used as timing reference points.

The invention considers either the detected change in impedance between the electrodes 24 and 28, or transit time associated with transit of a signal between a reference point and the distal ends 25 of the electrodes (see FIG. 4). Where the end of the secondary conductor is used as a reference point, then there are two segments of time, one between shoulder 73 and the end 64 of the conductor where it meets the electrode. The other is the segment along electrode 24 itself between the proximal end 67 and the distal end 25 of the electrodes. The permittivity of the first segment (between 73 and 67), and the permittivity of the second segment (between 67 and 25) is the measurement being taken by the system.

In an alternative system, the transit time from points 67 to 25 can be used if there is sufficient impedance change at point 67 to allow this point to be discerned from the time domain reflectometry traces. In either approach, the short time period between the signal reaching the proximal end 67 of primary electrode 24 and the time it reaches the distal end is a function affected by the average permittivity of the fluid mixture or other media held in channel 20 across which the sensor is detecting.

It has also been found that the permittivity of the fluid within channel 20 also has a noticeable effect on the impedance measured for the transition segment from shoulder 73 to proximal end 67 of the electrodes. Thus the capacitance of this segment also varies with the constituency of the fluid channel and calibration is needed to accurately determine the changes in reflected signal strength over various delay times as a function of the fluid in channel 20.

Figure 2:
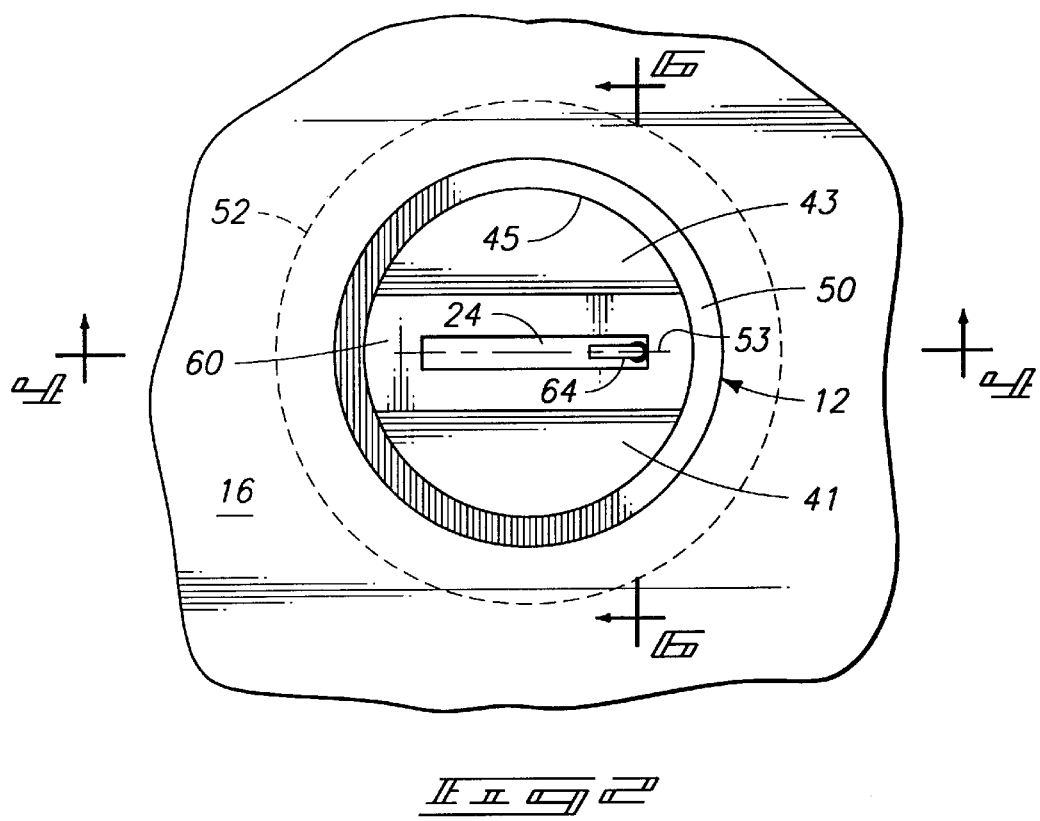
FIG. 2 is an end view of one cross-channel sensor forming part of the sensor system of FIG. 1.

FIG. 2 illustrates cross-channel probe 12 in end view as seen substantially flush-mounted in wall 16. More particularly, the orientation of primary electrode 24 within an end face of probe 12 is shown to extend substantially transverse to the direction of fluid flow within flow channel 20. Preferably, primary electrode 24 is seated within an insulator block 60 formed from a ceramic, or Teflon™ plastic, or other suitable insulators. Primary electrode 24 forms a thin conductor that is mounted in insulator block 60, along the surface, just under the surface, or along the surface with a coating (not shown) thereover. Sensing surface 26 and any over-layer are constructed and mounted to provide a substantially flush, or level, relation with the adjacent surface of insulator block 60 when received therein. Also preferably, insulator block 60 is formed from a substantially elongate and rectangular block of insulatory material which is received in a housing 50 about which additional insulating material is received. For example, block 60 is preferably formed from a ceramic material having sufficient resistance to erosion or ablatement, such as a high purity (99.99%) alumina or zirconia stabilized with magnesia may also be acceptable.

Block 60 and insulating pieces 41 and 43, in combination, cooperate to form a round insulating plug assembly that extends from the cylindrical shape of housing 50. Alternatively, parts 60, 41 and 43 can be a single piece of suitable material, such as alumina or zirconia with electrode 24 attached. Preferably, the diameter of probe housing 50, where it extends through wall 16, is in the range of 1.0 to 1.5 inches in diameter, with primary electrode 24 being embedded into the plug insulator block 60. This assembly can also be made from Teflon™ or other suitable dielectic and chemically resistant materials depending upon the service in which the assembly will be used.

Block 60 is designed to have a sufficient depth and width to allow the desired electric field to be developed by primary electrode 24. This is done in such a manner that the field will not be unduly affected by the surrounding metal of housing 50 and wall 16.

According to one construction, the conductor depth of primary electrode 24 is preferably in the range of 0.010 inches to 0.02 inches in thickness, with a geometry of 1.0 inches by 0.5 inches up to 1.0 inches by 0.75 inches in plan view, forming sensing surface 26 accordingly. Also according to this implementation, insulator block 60 is sized in the range of 0.2 to 0.3 inches in thickness, or depth, extending perpendicular to sensing surface 26. Preferably, insulator block 60, as well as insulating pieces 41 and 43, are formed from a ceramic material. Alternatively, any combination of Teflon™ or ceramics could be utilized. The conductor forming primary electrode 24 is preferably buried under the surface of insulating block 40 to allow it to be used in the detection of conductive fluids. Alternatively, the conductor of primary electrode 24 can be exposed where process conditions allow, or be coated with a coating material (not shown, also discussed below).

FIG. 4 illustrates the construction of sensing probe 12, enabling substantially flush mounting within a wall defining a fluid flow channel. It is to be understood that sensing probe 14 is similarly constructed, with the exception that the ground sheath 48 or other secondary conductor is electrically connected with the corresponding secondary electrode 28 (see FIGS. 1 and 3).

Probe 12 is preferably formed from a cylindrical metal housing member which is preferably sized by machining it to enable it to be received and fitted in sealed engagement with wall 16 (see FIG. 5). Housing member 50 is formed with an enlarged and circumferentially extending pressure seal flange 52 that cooperates to define a seal face 54 for mating with a complementary seat 104 within wall 16. Seal face 54 extends between pressure seal flange 52 and a cylindrical insert portion 56. Insert portion 56 is sized to be snugly received within a receiving bore 102 (see FIG. 5) such that primary electrode 24 is provided in a substantially planar relation with the inside surface of wall 16. When assembling housing 50 in a wall, an abutment surface 57 along side pressure seal flange 52 is engaged with a nut 17 in the form of a compression type screw ring configured to press the probe housing member 50 into the tapered seat 104 (see FIG. 5), forming a seal. A cylindrical nut guide 58 is formed by housing 50 about which such a screw ring nut 17 is received.

Primary electrode 24 is presented for mounting in substantially flush relation with a support wall of a fluid flow channel 22 by mounting electrode 24 within a ceramic insert 60 (see FIG. 5). Ceramic insert 60 is sized to be received within insert portion 56 of housing member 50 such that the conductive metal electrode 24 is electrically isolated from housing 50. As shown in FIG. 4, primary electrode 24 is further electrically coupled with center conductor 46 of lead line 32 by way of an intermediate conductor 62.

Conductor 62 preferably has an outer insulating cover 66 and a copper center, or central, conductor 64, as shown in FIG. 4. One end of conductor 64 extends through an aperture in ceramic insert 60 and a corresponding aperture in primary electrode 24 such that one end portion is folded over and brazed into electrically conductive relation with a recess in primary electrode 24. An opposite end portion of conductor 64 is brought into electrically conductive engagement with center conductor 46 by brazing or otherwise connecting them within the annular connector 76. Primary electrode 24 couples with center conductor 64 at proximal end 67 such that, when brazed together, they remain substantially flush within a receiving recess of ceramic insert 60. Hence, primary electrode 24 is presented in substantially flush relation with a wall in which probe 12 is received.

As shown in FIG. 4, center conductor 64 of conductive line 62 is supported for electrical connection with center conductor 46 by way of a split ceramic collar 70 and a transition insulator 74. Ceramic collar 70 and transition insulator 74 are configured to engage in inter-fitting relation, with center conductor 64 extending through a conductor aperture 72 of transition insulator 74. In this manner, center conductor 64 is presented and received within annular connector 76 such that center conductor 64 is presented in substantially collinear and adjacent relation with center conductor 46 where they are joined together.

Transition insulator 74 is further supported in coaxial relation within housing 50 by way of a stainless steel cylindrical ferrule 78 and a stainless steel mating cap 80. The joint between these two parts are preferably welded or brazed. A transition assembly 77 is formed by insulator 74, tube 76, ferrule 78 and cap 80 for providing electrical connection between electrode 24 and coaxial cable 32 and such assembly serves as a primary pressure boundary. Cap 80 is sized to receive lead line 32, with cap 80 being preferably welded or brazed to ground sheath 48 in electrically conductive relation. Stainless steel ferrule 78 is then received for coaxial insertion within cap 80, forming a rigid structural encasement that is electrically isolated and coaxially encircles center conductors 64 and 46 therein. A ceramic isolator 68 is provided for encircling the entire assembly, including ferrule 78, cap 80, and split ceramic collar 70, extending within housing 50. In this manner, electrical connection is made between center conductor 46 of lead line 32 and primary electrode 24, while electrically isolating ground sheath 48 from center conductor 64. Hence, the preceding forms transition assembly 77 so as to be positioned between coaxial cable 32 and primary electrode 24 to provide electrical connection between the coaxial cable conductor 46 and electrode 24.

In an alternative version, the transition insulator and related parts described above can be replaced with a Teflon™-filled, or similar suitable material-filled, coaxial line. This alternative construction does not require the specific construction indicated because the line will self-seal under many less severe service applications, such as water and many chemicals under low and moderate pressure conditions.

Additionally, a seal can advantageously be provided to prevent leakage through or about coaxial cable 32, by way of a coaxial gland 84 (FIG. 4). Gland 84 is formed by mating together a gland body member 86 and a suitably sized cap member 88. Gland body 86 forms a cylindrical surface having male threads at both ends. One end is received in threaded relationship with part 50. The other end is in threaded relationship with cap member 88 which has complementary female threads such that cap 88 and gland body 86 can be joined together. The joint between part 50 and gland body 86 can also be further sealed by welding, or it can be unthreaded and totally mounted by welding.

Cap 88 receives an insulating ferrule 90 that is sized to snugly receive lead line 32 therethrough. Ferrule 90 includes a seal part flange 92 which is held within a receiving chamber of gland body 86. These parts preferably have mating conical surfaces which are complementary and forced together by a follower sleeve 95 as cap 88 is screwed onto cap 86 and against follower 95.

In the above manner, lead line 32 can be sealed to housing 50 to prevent leakage in applications where there is pressurized fluid in flow channel 20. The transition assembly components or suitable substitutes enable electrical connection of center conductor 46 with primary electrode 24 through this sealed joint.

The construction shown in FIG. 4 is also suitable for electrically connecting cable 34 with secondary electrode 28 (of FIG. 1). In the case of the other probe 14, the construction of FIG. 4 is slightly modified such that the secondary conductor in the form of ground sheath 48 is electrically coupled with the center conductor 64 of intermediate conductor 62 by way of a stainless steel cylindrical ferrule (not shown) similar to that of ferrule 78, but which is sized to extend completely around split ceramic collar 70. Conductor 64 is brazed or mechanically engaged with ferrule 78 so as to provide electrically conductive engagement between secondary conductor 48 and the secondary electrode 28.

Electrodes 24 and 28 of FIGS. 1 and 3 are positioned relative to flow channel 20 so as to present sensing surfaces 26 and 30 for sensing the characteristics of fluid mixture 22. Mixture 22 serves as a dielectric disposed between face surfaces 26 and 30. However, it is sometimes preferred to deposit a dielectric coating on surfaces 26 and 30 to isolate electrodes 24 and 28 from the fluid mixture. Surface 26 may include an end portion of center conductor 64 which connects with electrode 24 using any suitable brazing/welding or other material used to join electrode 24 with conductor 64. The electrode 28 is connected to the sheath or second conductor 48. This is also accomplished in a suitable manner such as by brazing or welding.

The entire face surfaces are preferably coated with the electrodes 24 and 28 covered. More preferably, a dielectric layer (not shown) is provided to cover surfaces 26 and 30 in order to insulate and isolate the corresponding electrodes from the fluid mixture which helps to prevent dissipation or attenuation of the stimulating time domain reflectometry signal and the resulting reflected signals, particularly when fluid 22 is electrically conductive.

Teflon™ polymer (polytetrafluoroethylene) is one preferred material for forming the dielectric layer. Teflon™ is preferably applied to primary electrode 24 and secondary electrode 28, along sensing surfaces 26 and 30, respectively, by using a baked Teflon™ coating process, such as at a temperature of 750° F. The process results in a Teflon™ layer having a thickness of between 0.002 and 0.005 inches, preferably about 0.003 inches. The Teflon™ is applied after electrodes 24 and 28 are received within an insulator block 40, and before assembly within housing 50.

According to the construction of FIGS. 1–4, primary electrode 24 and secondary electrode 28 are preferably fabricated from a metal, metal alloy or other suitable electrically conductive material which is advantageously resistant to corrosion and erosion. A variety of materials are suitable. Hastel™ and Zircaloy™ are examples of suitable materials, with Zircaloy™ being preferred in high temperature, highly corrosive environments. Zircaloy™ is a trademark for a family of materials. A variety of Zircaloy™ alloys from this family can be used depending on the process conditions. "Zircaloy™4" is currently the most preferred for mineralized water and steam applications.

Oxidation is another method of providing a dielectric layer over portions or all of the electrodes 24 and 28. The preferred methods of oxidizing a Zircaloy™ electrode include subjecting it to steam in an autoclave at 400° C. at a pressure of 1,500 lbs. per square inch for approximately 48 hours. This process creates a zirconium oxide surface which is electrically non-conductive while also being highly resistant to corrosion. Such method is preferably implemented so as to coat electrodes 24 and 28, prior to assembly within ceramic insert 60 within housing 50 (of FIG. 4).

Oxides can alternatively be sputtered onto the surface of the primary and secondary electrodes. The resulting oxide coating is optionally hardened by subsequently treating the electrode in a vacuum furnace at 705° C. for two hours. The oxides will typically have thicknesses of 0.001–0.010 inches.

An alternative oxidation method involves anodizing the electrodes and center conductor 64 (see FIG. 4) before assembly of housing 50. The resulting anodized surface provides dielectric isolation between the electrodes and center conductor 64 in the fluid mixture. Anodization of a Zircaloy™ electrode is preferably accomplished in 0.05% sodium hydroxide at 150 volts for 30 minutes. The anodized surface is preferably removed over electrode surface areas to which components are to be welded. Alternatively, the components can be welded, then anodized and assembled within housing 50.

The coatings or layers described above can also be combined. For instance, one preferable dielectric layer is obtained by providing a Teflon™ coating over an anodized surface.

Tests indicate that a baked Teflon™ coating works well in applications where erosion of the electrode surface is not a problem and where fluid mixture temperatures are less than 550° F. The electrode of such a probe can be made of various nickel-based alloys to resist corrosion. Where a Teflon™ coating has very slight effect on probe impedance measurements, such an effect is constant and can be easily accounted for during calibration of the system. More importantly, the insulating properties of the Teflon™ or other dielectric layer or layers significantly reduce signal losses through attenuation where measurements are being taken in conductive fluid mixtures. In applications where erosion is a problem or where temperatures are greater than 550° F., an oxide coating is preferable to Teflon™. Such an oxide coating may be created by anodizing or autoclaving as mentioned above. Oxide layers have a similar effect on impedance measurements as does a Teflon™ coating.

FIG. 5 illustrates an exploded perspective view of the assembly of sensor probe 12 within the receiving bore 102 to provide primary sensor 24 in substantially flush relation with wall 16. Receiving bore 102 is sized to receive housing member 50 such that primary sensor 24 remains substantially flush, or level, with wall 16. Primary sensor 24 is supported within ceramic insert 60, in combination with blocks 41 and 43, for insertion within an aperture 45 of housing 50. Blocks 41 and 43 are also preferably formed from an insulatory material, such as a ceramic material, and engage in dovetail-fashion with ceramic insert 60, as discussed below in reference to FIG. 6. When assembled, blocks 41 and 43 and ceramic insert 60 form a cylindrical insert that is snugly and sealingly received within aperture 45. In this manner, primary electrode 24 is electrically insulated from metal housing 50. It is also possible for parts 60, 41 and 43 to be formed using a single block of Teflon™ or ceramic which is brazed or otherwise formed into place.

Also according to FIG. 5, the engagement of seal face 54 on housing 50 with corresponding seat 104 in wall 14 can be readily seen. More particularly, the threading engagement of the compression-type screw ring nut 17 into complementary threaded bore 106 of wall 16 will drive seal face 54 into engagement with seat 104, forming a seal therebetween. More particularly, a cylindrical end 96 of screw ring nut 17 is brought into engagement with housing 50. A hexagonal head 100 on screw ring nut 17 facilitates tightening with a wrench. A through bore 97 on screw ring nut 17 receives cylindrical section 58 therethrough. In this manner, lead line 32 and a portion of housing 50 are coaxially received within screw ring nut 17. The use of screw ring nut 17 to removably install and seal sensor probe 12 in wall 16 (as well as nut 19 to removably install and seal sensor probe 14 in wall 16) facilitates service and maintenance.

According to FIG. 6, intermediate conductor 62 is assembled to extend through ceramic insert 60, preferably with a tight, sealed fit. A pair of receiving slots 110 are also provided in either side of ceramic insert 60 so as to provide for interdigitating assembly with blocks 41 and 43 (of FIG. 5). Center conductor 64 of intermediate conductor 62 is received through a hole in a receiving depression of primary electrode 24 where it is then folded over and welded. The presence of recess 63 enables the substantially flush presentment and welding of center conductor 64 in relation to primary electrode 24. Hence, the substantially flush and smooth presentment of primary electrode 24 is provided within ceramic insert 60, and in assembly, with wall 16 (of FIG. 5).

The invention also includes novel methods. The methods include producing a series of time domain reflectometry signals. Such signals are generated at suitable intervals to allow the electrical pulse or pulses contained in the time domain reflectometry signals to transit the distance from the signal generator (not shown) to the point or points of reflection which generate reflected time domain reflectometry signals and then back to the signal detector contained in the time domain reflectometer. The time domain reflectometry circuitry senses or detects the reflected signals and measures the strength of the reflected signals. This is done repeatedly at different delay times in order to determine the impedance at various points along the conductor being tested. With this information the reflected signal strength and effective impedance at various distances down the line and connected probes are obtained. The measured voltage, or effective impedance derived therefrom, of the reflected signals allows the user to ascertain whether an impedance mismatch exists and the delay indicates the distance along the line at which the mismatch is occurring.

The methods further include conducting the series of time domain reflectometry signals along an electrically conductive signal line, such as signal line 36. The conducting of the time domain reflectometry signals is preferably done in a way which does not dissipate the signal during conduction. Although some losses are a necessary part of electrical signal propagation, the inventors preferably use a coaxial conductor, such as described above to reduce or minimize signal losses.

The methods further advantageously include bifurcating the time domain reflectometry signals between a first lead line, such as line 32, and a second lead line, such as line 34. The bifurcation of the stimulating signals is advantageously accomplished using an electrically conductive tee connection. Other means for bifurcation are also possible, however, at this time none are as desirable as the straightforward and reliable tee connection. Tee connection 38 is a suitable example.

The bifurcation of the stimulating signal forms time domain sub-signals. The time domain reflectometry sub-signals can each be considered as primary and secondary branch signals. The primary branch signals include first portions which are the active pulses which are conducted to the primary sensor electrode 24. The primary branch line 32 also carries any reactive signals which are induced in the secondary conductor as a result of the active pulses being conducted down the primary conductor of line 32. The secondary conductor maintains continuity in the impedance experienced by the stimulating time domain reflectometry signals. If the secondary conductor was terminated earlier in the circuit, then there would be an impedance change associated with the point at which the insulation sheath and surrounding secondary conductor are stopped. This is true because the surrounding insulation and secondary conductor have an effect upon the dielectric constant experienced by the active signal pulses as they progress down the center conductor of branch line 32. Such an impedance change would result in a significant reflection of the time domain reflectometry stimulation signal. The end of the secondary conductor of line 32 is ended within sensor 12, and even more preferably as close as practical to the electrode 24.

The secondary branch signals are conducted by the secondary branch line, such as line 34. The secondary conductor of branch line 34 conducts any reactive signal induced in the secondary conductor. Such reactive signals may be a result of direct induction from the active signal carried on the primary conductor of line 34, or line 36 which leads thereto. The active signal is propagated down the primary conductor of secondary branch line 34 to maintain continuity of the impedance of line 34, as explained above with regard to the primary branch line 32. The end of the primary conductor of line 34 is ended within sensor 14 without electrical connection to electrode 28. Even more preferably, the dead end of the primary conductor of secondary branch line 34 is ended as close as practical to the electrode 28 without achieving electrical contact.

Figure 7:
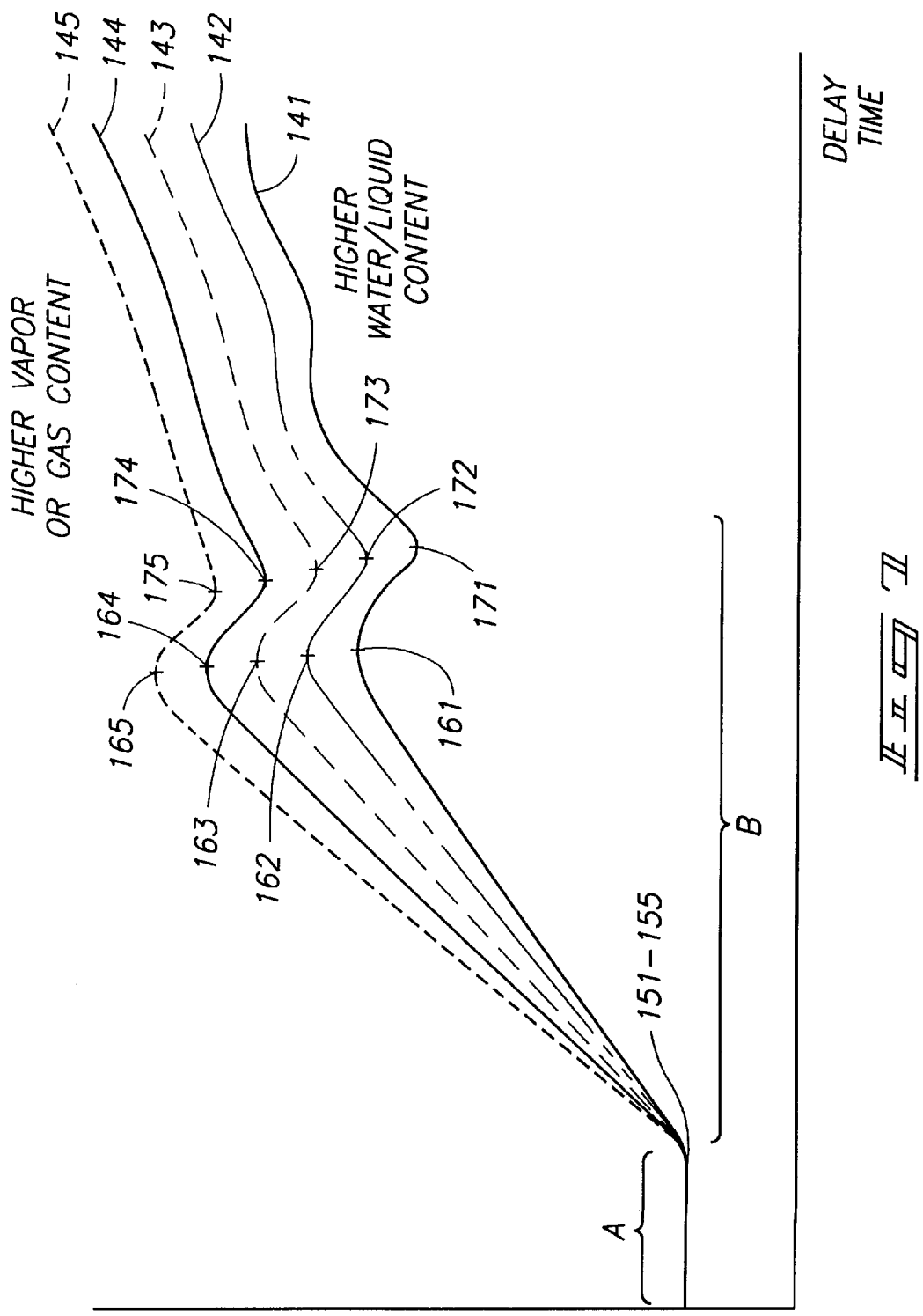
FIG. 7 is a graph showing system measurements for impedance for various delay times.

Methods according to this invention also include detecting reflected signals which return from the primary and secondary electrodes. The detecting can be done in several different ways according to known time domain reflectometry techniques. In essence the stimulating signals are send down line 36, through tee 38, and down each branch line 32 and 34. The time domain reflectometer sends numerous stimulation signals and then detects the amount of reflected signal which returns at various delay times to compile an estimate of the impedance along the lines. FIG. 7 show a graph having a series of traces or curves 141–145. Each curve indicates relative voltage of the reflected signals at various delay times. The relative voltage of the reflected signals also indicates the impedance as a function of delay time. The delay time indicated on the X-axis of these figures also translates into an indication of distance along the conductors 36, 32 and 34, and along the length of electrodes 24 and 28.

Curve 141 shows a plot wherein the flow channel is filled with a fluid mixture which is all or principally a gas or vapor, such as air, steam, mixtures thereof or other gases and vapors. The point labelled 151 is the start of the transition, such as at shoulder 73. The impedance increases from point 151 toward a high-point 161 which represents at or near the proximal end 67 of the electrode. The reflected signal 141 at greater delay times then shows decreases in the impedance from high-point 161 toward point 171 which represents the distal end 25 of the electrodes. Thereafter the associated impedance is relatively higher and is an artifact arising from reflection of the active and passive signals from the distal ends 25 of electrodes 24 and 28.

Curves 142–145 have generally similar shapes as curve 141 just described. Each curve has an associated high-point 162–165 indicating approximately the proximal end of the electrodes. Curves 141–145 show a decreasing dielectric constant experienced by the active and passive signals from curve 141 to curve 145. This is associated with decreasing proportions of water or other liquid in exchange for increasing gas or vapor in the fluid mixture being tested. Thus curve 141 represents a curve for a fluid mixture which is more water and curve 145 represents a curve for a fluid mixture which is more gas or vapor.

An decrease in the dielectric constant has an associated effects of increasing the velocity of the electrical pulse being conveyed and decreasing the transit period to and from a particular point along the time domain reflectometry signal path. Decreasing dielectric constant (decreasing permittivity) also increases the apparent impedance and reflected signal voltage experienced in the transition and electrode portions of the curves, such as at points 161 and 171 as compared to points 165 and 175 which show higher impedance and higher reflected voltage signals.

The relative proportions of gas or vapor relative to the water, liquid or other mixture can be determined in two different approaches. One approach utilizes the measured impedances at the electrodes, or electrodes and transition portions of the signal. Another approach considers the relative transit times associated with the signals. Both will be discussed below.

The length along the X-axis of the time segment between points 161 and 171 indicates the time needed to transit the electrodes 24 and 28 between the proximal and distal ends thereof. The period of time varies as a function of the square roots of the permittivities of the fluid in channel 20. An example is air which has a permittivity of 1 at ambient temperatures and pressures. Water has a permittivity of approximately 80 at ambient temperatures and pressures. Thus the impedance difference between an all air sample versus an all water sample will vary by the square root of 80 divided by the square root of 1, or a factor of approximately 9 times.

The equation relating these transit times is of the general form:

total transit time=transit time for segment A+transit time for segment B

Transit time for segment A is determined from calibration measurements and remains a factor in the equation as used with a particular set of sensors and their installation. Recalibration may be needed periodically.

Transit time for segment B is the transit time between the proximate and distal ends of electrodes 24 and 28. This is a component of the measured transit time.

The transit time for segment B is estimated by deriving such from the total transit times being detected measured using the time domain reflectometry system. This is done by using the above relationships and calibration testing with materials with known dielectric constants, such as air and water. With such calibration testing the value of transit time B is known or closely estimated. Therefore the transit time for segment A can be calculated. The transit time for segment A does not typically vary in a significant manner between calibration testing of the system and normal data acquisition. This provides the basis for determining and estimating the transit time for segment A. Once the transit time for segment A is sufficiently estimated, then the measured total transit times can be used in the calculating of approximate transit times for segment B.

The transit times for segment B are used to estimate the dielectric constant detected between sensor electrodes 24 and 28 during the testing. The derived dielectric constant measurement relates to other similar measurements with different materials as the ratio of the square roots of the dielectric constants. For example the ratio in transit times between a channel filled with air might be represented by the following:

$$\frac{(\text{transit time for segment } B \text{ air})^{1/2}}{(\text{transit time for segment } B \text{ water})^{1/2}}$$

This type of calculation is then used to determine the type or proportion of material or materials present between the electrodes during testing.

Due to the relative difficulty of defining the starting point of the electrode it may be difficult to quantitatively determine the relative periods of time. This occurs because the permittivity changes occur in the transition portion of the probes as well as at the actual electrode surfaces. Thus, to date, the relative impedance values at the electrode segment of the reflected signals has been found to be a more reliable measure of the relative proportions of the constituents contained in the fluid mixture being sensed.

The relationship of relative impedance values is also a square root relationship. Impedance Z relates to dielectric constant C between two cases in the following relationship:

$Z_1$ is proportional to $1/(C_1)^{-1/2}$ $Z_2$ is proportional to $1/(C_2)^{-1/2}$ Thus $Z_1$ and $Z_2$ are related in the following equation:

$Z_1/Z_2 = (C_2)^{-1/2}/(C_1)^{-1/2}$

This indicates that as the dielectric constant increases for water ($C_2$) versus ($C_1$) then the impedance increases for air ($Z_1$). This is shown by FIG. 7 where the higher concentrations of air are shown with curve 145 and such has higher impedance values.

The novel methods of this invention further include calibrating a sensor system such as described above. The calibrating includes deriving an estimated transit time A which is used to correct or interpret the total transit time and derive an estimated transit time B.

The methods can further include deriving a measure of dielectric constant or permittivity experienced between the probes 12 and 14. This deriving can be in turn used in identifying the proportions or presence of at least one variable constituent present in the flow channel between the electrodes. The system shown is also advantageous in allowing such determinations to be made as a flowing fluid passes between the sensor 24 and 28 and without requiring that the flow be stopped or otherwise be modified or abridged in any significant fashion.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. A sensor system for use with time domain reflectometry systems to allow measurement of a fluid mixture within a fluid channel having constituents with differing electrical permittivities, comprising:

a first sensor having a first sensor housing; said first sensor being mountable upon a first side of the fluid channel with an inside face thereof which is directed toward the fluid channel;

at least one primary electrode made from electrically conductive material and having a sensing surface which is alone the inside face of the first sensor, the at least one primary electrode serving to conduct a pulsed time domain reflectometry signal along the sensing surface of the at least one primary electrode;

a second sensor having a second sensor housing; said second sensor being mountable upon a second side of the fluid channel with an inside face thereof directed toward the fluid channel in opposing relationship to the inside surface of said first sensor;

at least one secondary electrode made from electrically conductive material and having a sensing surface which is along the inside face of the second sensor;

a first lead connected to the first sensor in electrical communication therewith, said first lead having a primary conductor and a secondary conductor, said first lead primary conductor being electrically connected to the at least one primary electrode;

a second lead connected to the second sensor in electrical communication therewith, said second lead having a primary conductor and a secondary conductor, said second lead secondary conductor being electrically connected to the second electrode;

a signal bifurcation connector for connecting to said first lead and said second lead at the primary and secondary conductors thereof, said signal bifurcation connector further having a main lead connection for connecting to a main lead through which time domain reflectometry signals are conveyed to and from the first and second sensors.

2. A sensor system according to claim 1 and further comprising at least one dielectric layer covering either of said sensing surfaces of the at least one primary electrode or at least one secondary electrode, for electrically isolating at least one of the electrodes from the fluid mixture.

3. A sensor system according to claim 1 wherein the at least one primary and secondary electrodes have elongated sensing surfaces.

4. A sensor system according to claim 1 and further comprising at least one transition assembly providing electrical connection with at least one of said primary or secondary electrodes, and providing at least one seal to aid in preventing fluid leakage about said at least one of said primary or secondary electrodes.

5. A sensor system according to claim 1 and further comprising at least one transition assembly providing electrical connection with at least one of said primary or secondary electrodes, the transition assembly including a transition insulator and an intermediate conductor which is in sealed relationship received through the transition insulator to seal the sensor from the fluid mixture.

6. A sensor system according to claim 1 wherein the first lead and second lead are approximately the same length and have approximately the same impedance.

7. A sensor system according to claim 1 and further comprising at least one dielectric layer covering at least the sensing surface of the at least one primary electrode, for electrically isolating the primary electrode from the fluid mixture and preventing dissipation of a time domain reflectometry signal propagated to the sensor system.

8. A sensor system according to claim 7 wherein the at least one dielectric layer is an oxide layer formed upon the sensing surface of the at least one primary electrode.

9. A sensor system according to claim 7 wherein the at least one dielectric layer covers portions of the at least one secondary electrode to electrically isolate the at least one secondary electrode from the fluid mixture and to further prevent dissipation of a time domain reflectometry signal.

10. A sensor system according to claim 1 and further comprising a main lead signal cable having a primary conductor which is electrically connected to the primary electrode and a secondary conductor which is electrically connected to the secondary electrode.

11. A sensor system according to claim 10 and further defined by said main lead signal cable being matched to have an impedance approximately equal to the combined impedances of the first and second leads.

12. A sensor system according to claim 1 further comprising a main lead signal cable having a primary conductor which is electrically connected to the primary electrode and a secondary conductor which is electrically connected to the secondary electrode, said main lead signal cable being matched to have an impedance approximately equal to the combined impedances of the first and second leads.

13. A sensor system according to claim 12 wherein the first lead and second lead are approximately the same length.

14. A sensor system according to claim 1 and further comprising a vessel which defines the fluid channel therein; and wherein the first and second sensors are mounted with said inside faces in opposing juxtaposition relative to one another across the fluid channel.

15. A sensor system according to claim 14 wherein the sensing surfaces of said at least one primary electrode and the sensing surfaces of said at least one secondary electrode are parallel.

16. A sensor system according to claim 14 wherein the sensing surfaces of said at least one primary electrode and the sensing surfaces of said at least one secondary electrode are aligned in a plane.

17. A sensor system according to claim 1 wherein the sensing surfaces of said at least one primary electrode and the sensing surfaces of said at least one secondary electrode are parallel and are aligned in the same plane.

18. A sensor system according to claim 17 and wherein the first sensor and second sensor are approximately axially aligned across the fluid channel.

19. A complementary pair of sensors used in a sensor system for time domain reflectometry measurement of a fluid having constituents with differing electrical permittivities, comprising:

a first sensor having a first sensor housing and an inside face which is directed toward the fluid during operation;

at least one primary electrode made from electrically conductive material and having a sensing surface which is along the inside face of the first sensor, the at least one primary electrode serving to conduct pulsed time domain reflectometry signals along the sensing surface of the at least one primary electrode;

a second sensor having a second sensor housing and an inside face which is directed toward the fluid during operation;

at least one secondary electrode made from electrically conductive material and having a sensing surface which is along the inside face of the second sensor;

a first lead connected to the first sensor in electrical communication therewith, said first lead having a primary conductor and a secondary conductor, said primary conductor of the first lead being electrically connected to the at least one primary electrode;

a second lead connected to the second sensor in electrical communication therewith, said second lead having a primary conductor and a secondary conductor, said secondary conductor of the second lead being electrically connected to the second electrode.

20. A complementary pair of sensors according to claim 19 and further comprising at least one dielectric layer covering said sensing surfaces of the at least one primary electrode and at least one secondary electrode, for electrically isolating the electrodes from the fluid mixture.

21. A complementary pair of sensors according to claim 19 wherein the at least one primary and secondary electrodes have elongated sensing surfaces.

22. A complementary pair of sensors according to claim 19 and further comprising at least one transition assembly providing electrical connection with at least one of said primary or secondary electrodes, and providing at least one seal to aid in preventing fluid leakage about said at least one of said primary or secondary electrodes.

23. A complementary pair of sensors according to claim 19 and further comprising at least one transition assembly providing electrical connection with at least one of said primary or secondary electrodes, the transition assembly including a transition insulator and an intermediate conductor which is in sealed relationship received through the transition insulator to seal the sensor from the fluid mixture.

24. A complementary pair of sensors according to claim 19 wherein the first lead and second lead are approximately the same length and have approximately the same impedance.

25. A complementary pair of sensors according to claim 19 and further comprising at least one dielectric layer covering at least the sensing surface of the at least one primary electrode, for electrically isolating the primary electrode from the fluid mixture and preventing dissipation of a time domain reflectometry signal propagated to the sensor system.

26. A complementary pair of sensors according to claim 25 wherein the at least one dielectric layer is an oxide layer formed upon the sensing surface of the at least one primary electrode.

27. A complementary pair of sensors according to claim 25 wherein the at least one dielectric layer covers portions of the at least one secondary electrode to electrically isolate the at least one secondary electrode from the fluid mixture and to further prevent dissipation of a time domain reflectometry signal.

28. A complementary pair of sensors according to claim 19 and further comprising a main lead signal cable having a primary conductor which is electrically connected to the primary electrode and a secondary conductor which is electrically connected to the secondary electrode.

29. A complementary pair of sensors according to claim 28 and further defined by said main lead signal cable being matched to have an impedance approximately equal to the combined impedances of the first and second leads.

30. A complementary pair of sensors according to claim 19 further comprising a main lead signal cable having a primary conductor which is electrically connected to the primary electrode and a secondary conductor which is electrically connected to the secondary electrode, said main lead signal cable being matched to have an impedance approximately equal to the combined impedances of the first and second leads.

31. A complementary pair of sensors according to claim 30 wherein the first lead and second lead are approximately the same length.

32. A complementary pair of sensors according to claim 19 and further comprising a vessel which defines the fluid channel therein;

and wherein the first and second sensors are mounted with said inside faces in opposing juxtaposition relative to one another across the fluid channel.

33. A complementary pair of sensors according to claim 32 wherein the sensing surfaces of said at least one primary electrode and the sensing surfaces of said at least one secondary electrode are parallel.

34. A complementary pair of sensors according to claim 32 wherein the sensing surfaces of said at least one primary electrode and the sensing surfaces of said at least one secondary electrode are aligned in a plane.

35. A complementary pair of sensors according to claim 19 wherein the sensing surfaces of said at least one primary electrode and the sensing surfaces of said at least one secondary electrode are parallel and are aligned in the same plane.

36. A complementary pair of sensors according to claim 35 and wherein the first sensor and second sensor are aligned across the fluid channel.

* * * * *